United States Patent [19]

Nishida et al.

[11] Patent Number: 5,674,732
[45] Date of Patent: Oct. 7, 1997

[54] RAPAMYCIN PRODUCER

[75] Inventors: Hiroyuki Nishida, Handa; Tatsuo Sakakibara, Chita-gun; Yuji Yamauchi; Taisuke Inagaki, both of Handa; Yasuhiro Kojima, Nishio; Nakao Kojima, Nagoya, all of Japan

[73] Assignee: Pfizer Inc., New York, N.Y.

[21] Appl. No.: 325,378

[22] PCT Filed: Feb. 26, 1993

[86] PCT No.: PCT/US93/01534

§ 371 Date: Oct. 26, 1994

§ 102(e) Date: Oct. 26, 1994

[87] PCT Pub. No.: WO93/22446

PCT Pub. Date: Nov. 11, 1993

[30] Foreign Application Priority Data

Apr. 27, 1992 [JP] Japan .................................. 4-107612
Dec. 2, 1992 [JP] Japan .................................. 4-323407

[51] Int. Cl.[6] .................................................. C12N 1/20
[52] U.S. Cl. .................. 435/252.1; 435/119; 435/72.1; 435/117; 435/111
[58] Field of Search .................. 435/252.1, 119, 435/72.1, 117, 118

[56] References Cited

FOREIGN PATENT DOCUMENTS 177771   4/1986   European Pat. Off. .
403242   12/1990  European Pat. Off. .

OTHER PUBLICATIONS

Rose, A. H. "Industrial/Microbiology", Butter-Worths, London, 1961, pp. 191–193.

Primary Examiner—Irene Marx
Attorney, Agent, or Firm—Peter C. Richardson; Paul H. Ginsburg; B. Timothy Creagan

[57] ABSTRACT

The present invention provides a novel culture which belongs to Actinoplanes (Actinoplanes sp. FERM BP-3832). This culture is capable of producing rapamycin more than ten times efficiently than the cultures which have been reported (e.g., Streptomyces hygroscopicus ATCC 29253). The present invention provides a process for the production of rapamycin which comprises cultivating Actinoplanes sp. FERM BP-3832 and thereafter isolating rapamycin from the fermentation mixture.

2 Claims, No Drawings

RAPAMYCIN PRODUCER

This application was filed under 35 USC 371 as the national phase of PCT/US93/01534.

TECHNICAL FIELD

This invention relates to a new culture capable of producing rapamycin. Rapamycin of the present invention is produced by fermentation of a new microorganism designated as Actinoplanes sp. N902-109 (FERM BP-3832) in a nutritious medium.

BACKGROUND ART

Rapamycin (U.S. Pat. No. 3929992 and No. 3993749) was reported as an antifungal antibiotic which was produced by Streptomyces hygroscopicus AY B-994 (ATCC 29253) (C. Vezina, A. Kudelski and S. N. Sehgal, J. Antibiotics 28,721-726, 1975). In recent years, it has been demonstrated that rapamycin shows potent immunosuppressive activity. Hitherto, it is known that S. hygroscopicus ATCC 29253 is used for the production of rapamycin, which was reported together with physicochemical properties (U.S. Pat. No. 3929992). An object of the present invention is to provide a new culture which belongs to the different genus from Streptomyces. In addition, an object of the present invention is to provide a culture capable of producing rapamycin more efficiently than the cultures which have been reported in the prior art.

BRIEF DISCLOSURE OF THE INVENTION

The present invention is directed to a new culture capable of producing rapamycin. Rapamycin is produced by fermentation of Actinoplanes sp. N902-109 (FERM BP-3832).

The present invention also is directed to a culture capable of producing rapamycin more efficiently than Streptomyces hygroscopicus which has been reported in the prior art.

Furthermore, the present invention is directed to a biologically-pure culture having the characteristics of Actinoplanes sp. N902-109 (FERM BP-3832), as well as mutants and transformants of any of the foregoing, capable of producing rapamycin, including any such culture in freeze-dried form. Such a culture is capable of producing rapamycin in a recoverable quantity upon fermentation in an aqueous nutrient medium comprising assimilable sources of carbon and nitrogen.

DETAILED DESCRIPTION OF THE INVENTION

A culture N902-109 was isolated from a soil sample collected in Shizuoka Prefecture, Japan. The culture has narrow hyphae of the Actinomycetales and motile spores produced in sporangia-like clusters on the substrate mycelium—a feature characteristic of members of the genus Actinoplanes. The generic identity was further supported by the results of whole-cell analysis.

The taxonomical properties of N902-109 are as follows. The culture N902-109 was planted from a slant into ATCC #172 broth and grown for 4 days at 28° C. on a shaker. It was then centrifuged for 20 minutes, washed 3 times with sterile water and planted on media commonly used for identification of members of the Actinomycetales. The culture was incubated at 28° C. and the results were read at varying times but most commonly were taken at 14 days. The colors were described in common terminology, but exact colors were determined by comparisons with color chips from Color Harmony Manual, 4th Ed. The methods of whole-cell amino acid and sugar analyses are those described in Becker, B. et al., Appl. Microbiol., 12, 421–423, 1964, and in Lechevalier, M. P., J. Lab. Clin. Med., 71, 934–944, 1968.

Identification media used for the characterization of the culture and references for their composition are as follows:

1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p.331.
11. Nutrient Agar—Ibid, medium no. 14, p. 330.
12. Gordon and Smith's Tyrosine Agar—R. E. Gordon and M. M. Smith, J. Bacteriol., 69, 147–150, 1955.
13. Casein Agar—Ibid.
14. Calcium Malate Agar—S. A. Waksman, Bacteriol. Rev., 21, 129, 1957.
15. Gelatin—R. E. Gordon and J. M. Mihm, J. Bacteriol., 73, 15–27, 1957.
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M.P. Lechevalier, J. Lab. and Clinical Med., 71, 934–944, 1968, but use only 30 g potatoes, 2.5 g carrots and 20 g agar.
20. 2% Tap Water Agar.
21. Gauze's #1 Mineral Agar—G. F. Gauze et al., Problems in the Classification of Antagonistic Actinomycetes, English Ed., p.13, 1957.
22. Gauze's #2 Organic Agar—Ibid.
23. M3 Agar—T. J. Rowbotham and T. Cross, J. Gen. Microbiol., 100, 231–240, 1977.
24. Skim Milk—Difco.
25. Cellulose Utilization—a) H. L. Jensen, Proc. Linn. Soc., N.S.W., 55, 231–248, 1930. b) M. Levine and H. W. Schoenlein, A Compilation of Culture Media, medium no. 2511, 1930.
26. Carbohydrate Utilization—ISP #9 medium, Difco; G. M. Luedemann and B. Brodsky, Antimicrob. Agents and Chemother., 1964, 47–52, 1965.
27. Temperature Range—(ATCC medium 172).

1. The Growth Condition on Each Medium

Yeast Extract-Malt Extract Agar—Growth good, orange (4 la, 4 lc); raised, wrinkled, no aerial mycelium; reverse orange (4 la, 4 na); soluble pigment yellowish brown (3 lc).

Oatmeal Agar—Growth moderate, pale orange yellow (3 ea, 4 ea); slightly raised, smooth, no aerial mycelium; reverse same as surface; soluble pigment pale yellowish (2 ea).

Inorganic Salts-Starch Agar—Growth moderate, bright orange (4 ia), with some red dots (6½ ne); slightly raised, smooth, no aerial mycelium; reverse bright orange (4 ia); no soluble pigment.

Glycerol-Asaragine Agar—Growth poor to moderate, orange yellow (3 ga, 3 ia); thin, smooth, no aerial mycelium; reverse same as surface; no soluble pigment.

Czapek-Sucrose Agar—Growth moderate, pale pink to pale lavender (5 ca, 5 gc) with red dots (6 le, 6 pi); thin, smooth, no aerial mycelium; reverse same as surface; no soluble pigment.

Glucose-Asparagine Agar—Growth moderate to good, bright orange (4 na); slightly raised, smooth to granular, no aerial mycelium; reverse bright orange (4 na, 4 la); no soluble pigment.

Gordon and Smith's Tyrosine Agar—Growth moderate, dark brown (5 lg); slightly raised, smooth to granular, no aerial mycelium; reverse brown to dark brown (4 le, 5 lg, 5 ni); soluble pigment dark brown (5 ni).

Casein Agar—Growth good, orange to dark orange (5 la, 5 nc); moderately raised, wrinkled, no aerial mycelium; reverse same as surface; soluble pigment yellowish brown (3 ic).

Bennett's Agar—Growth good, orange to dark orange (5 la, 5 nc, 5 pc); raised, wrinkled, no aerial mycelium; reverse same as surface; soluble pigment yellowish brown (3 nc).

Emerson's Agar—Growth good, yellowish orange (4 la, 4 ia, 4 Ic); raised, wrinkled, no aerial mycelium; reverse same as surface; no soluble pigment.

Nutrient Agar—Growth poor, orange yellow (3 ga, 3 ia) with some orange to red dots (4 la, 5 la, 6 ne, 6 pg); thin, smooth, no aerial mycelium; reverse same as surface; no soluble pigment.

Calcium Malate Agar—No growth.

Potato Carrot Agar—Growth moderate, pale orange to brown (5 ea, 5 gc, 4 lc, 5 le); slightly raised, smooth, no aerial mycelium; reverse pink orange to orange (5 ea, 4 ia); soluble pigment pale pink (4 ca).

Tap Water Agar—Growth poor, pale orange yellow (3 ca); thin, smooth, no aerial mycelium; reverse same as surface; no soluble pigment.

Gelatin Agar—Growth moderate, orange (4 ga); slightly raised, smooth to granular, no aerial mycelium; reverse same as surface; no soluble pigment.

Starch Agar—Growth moderate to good, brown (5 le); moderately raised, smooth to slightly wrinkled, no aerial mycelium; reverse same as surface; soluble pigment pale yellowish (2 ea).

M3 Agar—Growth poor to moderate, cream (2 ca), but may become pale orange (3 ea, 3 ga) upon age; slightly raised, smooth, or appearing as isolated colonies, no aerial mycelium; reverse same as surface; no soluble pigment.

Gauze's #1 Mineral Agar—Growth moderate to good, orange to dark orange (4 ia, 4 nc); slightly raised, smooth to granular, no aerial mycelium; reverse same as surface; soluble pigment yellowish (2 ea, 2 ia).

Gauze's #2 Organic Agar—Growth good, bright orange (5 la, 4 na); raised, wrinkled, no aerial mycelium; reverse same as surface; soluble pigment yellowish brown (3 lc).

2. Morphological Properties

The morphological properties were observed on M3 agar after 3 weeks of incubation: hyphal masses produced, globose, subglobose, oval, elliptical to irregular, 4–20 μm diam., often coalesce into irregular masses, consisting of coiled hyphae or irregularly compressed hyphal masses or of spore clusters; spore clusters globose to subglobose, 3.5–8 μm diam., apparently containing no wall; spores globose, oval to elliptical, 1–1.2 μm diam., or 1–1.8×0.9–1.2 μm, motile, especially when suspended in 1% sucrose solution.

They were also observed on oatmeal agar after 5 weeks of incubation: hyphal masses produced, globose, oval, elliptical, or irregular, of various sizes, not producing spores when squeezed; substrate mycelium branched, 0.5–1.0 μm diam., conidiophores absent or if present monopodially branched; 1–3×0.4–0.6 μm; conidia borne singly, sessile or on a short conidiophore, globose, oval to elliptical, 1.0–1.8 μm diam., or 1.2–1.8×1.0–1.2 μm.

Hyphal masses were produced on yeast extract-malt extract agar, inorganic salts-starch agar, glycerol-asparagine agar, glucose-asparagine agar, Czapek-sucrose agar, potato carrot agar, tap water agar, gelatin agar, M3 agar, and Gauze's #1 mineral agar.

Spore-cluster production was moderate on M3 agar, oatmeal agar, Gauze's #1 mineral agar; poor on yeast extract-malt extract agar, glycerol-asparagine agar, casein agar; and none on the other media used.

3. Biochemical Properties

Melanin not produced; hydrogen sulfide not produced; gelatin liquefied; starch hydrolyzed; nitrate not reduced to nitrite; good growth but no disintegration on both Jensen's cellulose broth and Levine and Schoenlein's cellulose broth; coagulation and clearing on milk; casein digestion positive; and tyrosine digestion none to weak.

Carbohydrate Utilization: Glucose, arabinose, fructose, mannitol, sucrose, xylose, cellobiose, galactose, glycerol, lactose, mannose, salicin, soluble starch, and trehalose utilized; raffinose and melibiose doubtfully utilized; inositol, rhamnose, adonitol, dulcitol, erythritol, melezitose, α-methyl-D-glucoside, ribose, sorbitol, and sorbose not utilized.

| 4. Temperature Relations | | | |
|---|---|---|---|
| 21° C. | 28° C. | 37° C. | 45° C. |
| Good Growth | Excellent Growth | Excellent Growth | No Growth |

5 Cell Wall Analysis

The whole-cell hydrolysates contained meso-diaminopimelic acid, galactose, mannose and ribose.

Summarizing the above taxonomic properties, the culture N902-109 is characterized by the orange to bright orange substrate mycelium, the irregularly shaped hyphal masses on the substrate mycelium, and the motile spores which are born in sporangia-like clusters. Conidia may be produced singly on the substrate mycelium. The aerial mycelium was absent. The substrate mycelium mostly ranged from orange yellow, orange, bright orange to dark orange; it was brown on tyrosine agar and starch agar, and pale pink to pale lavender on Czapek-sucrose agar. The soluble pigment, if present, was pale yellow to yellow brown. The whole-cell hydrolysates revealed the presence of meso-diaminopimelic acid, galactose, mannose and ribose. The fact that spores are produced in sporangium-like clusters and are motile places the culture in the genus Actinoplanes.

This is the first report that rapamycin is produced by actinomycetous genera other than Streptomyces. In 1975 Vezina et al. reported that S. hygroscopicus AY B-994 (ATCC 29253) produced the antifungal antibiotic rapamycin (C. Vezina, A. Kudelski and S. N. Sehgal, J. Antibiotics 28, 721–726, 1975).

The many globoid or irregular hyphal masses produced on the surface of the agars resemble sporangia. However, upon a long incubation of up to five weeks, these masses never produced spores characteristic of those of Actinoplanes. The scarce to moderate production of the single conidia on the substrate mycelium are rare among members of Actinoplanes. Conidia produced singly, in chains, or in clusters have been reported in A. utahensis, A. armeniacus, and A. philippinensis, respectively.

The sporangia-like spore clusters appear to lack a wall. It is possible that sporangial wall may disintegrate as soon as spores are formed or that the wall fails to develop when spores mature. In this connection, it is interesting that Willoughby (J. Gen. Microbiol. 44, 69–72, 1966) described an Actinoplanes sp. which is characterized by a filed arrangement of spores both in sporangia and conidiophores systems. The small conidiophore systems resemble the spore clusters of the culture N902-109.

When compared with known species of Actinoplanes, the culture N902-109 resembles A. kanagawaensis (JP 58-32893 issued Feb. 25, 1983), A. missouriensis Couch, A. auranticolor (Couch) Palleroni, and A. teichomyceticus Parenti, Beretta, Berti & Arioli. However, it differs from A. kanagawaensis and A. auranticolor in the failure to produce hydrogen sulfide, the ability to coagulate milk, and the failure to utilize rhamnose. It is different from A. missouriensis in its failure to reduce nitrate and its failure to utilize rhamnose. Although it shares the same pattern of carbohydrate utilization with A. teichomyceticus, it differs by the smaller sporangia (spore clusters) and spores, the failure to produce melanin and hydrogen sulfide, the failure to reduce nitrate, and the ability to coagulate milk.

On the basis of the data mentioned above, the culture N902-109 is considered as a strain of the genus Actinoplanes and designated as Actinoplanes sp. It has been deposited at the Fermentation Research Institute, Agency of Industrial Science and Technology, 1-1-3 Higashi-tsukuba, Ibaragi 305, Japan, assigned as Actinoplanes sp. N902-109 with an accession number FERM BP-3832 under the Budapest Treaty on Apr. 13, 1992.

The inventors have discovered that the novel culture of genus Actinoplanes produces rapamycin. In addition, the productivity of the culture is better than that of S. hygroscopicus ATCC 29253.

It is well known that variants and mutants of members of Actinoplanes are easily obtained by natural selection or by artificial treatments. Thus, the invention is not limited to the use of Actinoplanes sp. N902-109 FERM BP-3832 herein described, but includes all cultures of Actinoplanes which produce rapamycin.

Fermentation of Actinoplanes sp. N902-109 is carried out as follows. In small scale fermentations, Actinoplanes sp. N902-109 is inoculated in sterilized medium, preferably grown at 26° C. for 2 to 10 days under submerged conditions with agitation and aeration. Larger scale fermentations may be carried out as follows. Actinoplanes sp. N902-109 is inoculated in sterilized medium, preferably grown at a temperature from 20° C. to 40° C. and at pH 5 to 9, more preferably from 6 to 8 for 2 to 10 days under submerged conditions with agitation (from 0 to 2,000 rpm more preferably from 100 to 360 rpm) and aeration (from 0 to 500%, more preferably from 80 to 120% volume of medium) in a medium.

Rapamycin of the invention is obtained from fermentation broth of Actinoplanes sp. N902-109 and can be separated by any conventional extraction and various techniques of chromatography. Though the rapamycin, in general, is slightly soluble in water, it is easily soluble in organic solvents. Thus, rapamycin can be separated by the difference of partition coefficient. For example, the whole fermentation broth is partitioned between water and organic solvent such as chloroform, ethyl acetate, methyl isobutyl ketone. The extract is dried over drying agent (e.g., $MgSO_4$, $Na_2SO_4$) and concentrated. The residue dissolved in adequate solvent is chromatographed to separate rapamycin by eluting with solvents (the sole solvent or more than two kinds of solvents with various ratios). The many kinds of powder solid such as silica gel, reverse-type silica gel and dextran can be used as supports or stationary phase. The high performance liquid chromatography (HPLC) is advantageous for separating rapamycin. In addition, the separation is also accomplished by a combination of the HPLC and the thin layer chromatography (TLC) methods. Rapamycin can be separated and purified by adopting methods well-known in the art.

Rapamycin can be confirmed by measuring anti-Candida albicans activity and the mixed lymphocyte reaction (MLR) activity as well as various analytical data.

The $IC_{50}$ values (µg/ml) of MLR and cytotoxicity for rapamycin were $7\times10^{-3}$ and >3.0, respectively when tested by standard procedures for MLR (D. P. Dubey et al., Manual of Clinical Laboratory Immunology, 3rd Ed., pp. 847–858, 1986) and for cytotoxicity (T. Mosmann, J., J. Immunol. Methods, 65, 55–63, 1983).

Antifungal activity was determined by an agar plate dilution method using a fungal culture, Candida albicans. The diameter of inhibition zone of rapamycin was 25 mm when tested at 40 µg/disk (8 mm diameter paper disk, Advantic) on an commercially available agar medium for neomycin assay (Difco).

The physicochemical data of rapamycin which was obtained hereupon were as follows:

(1) Appearance: White powder (2) UV max (nm): 267, 277, 288 (in MeOH)

(3) LSIMS ($C_{51}H_{79}NO_{13}$, m/z): 936.5546 $[M+Na]^+$ (4) NMR spectrum, IR spectrum: These data were in good agreement with those of the authentic rapamycin.

UV spectra were recorded on a JASCO Ubest-30 spectrophotometer. The NMR spectra were obtained with a JEOL GX270 magnetic resonance spectrometer. The IR spectra were obtained with a Shimadzu IR470 spectrophotometer. The mass spectra were measured on a Kratos Concept 1S mass spectrometer in the LSI (liquid Secondary Ion) mode using sodium iodide matrix containing a mixture of dithiothreitol and dithioerythritol (3:1).

The following examples are given for the purpose of illustrating the present invention and should not be construed as being limitations on its scope.

EXAMPLE 1

One hundred ml of Medium-1 (glucose 2%, polypeptone 0.5%, beef extract 0.3%, yeast extract 0.5%, blood meal 0.3%, wheat gluten 0.5%, $CaCO_3$ 0.4%, pH 7.0–7.2) in a 500 ml flask was inoculated with a slant culture of Actinoplanes sp. N902-109. The flask was shaken at 26° C. for 4 days on a rotary shaker with 7-cm throw at 220 rpm.

Five shake flasks containing the same medium (150 ml) were inoculated with 7.5 ml of the grown culture. These flasks were shaken at 26° C. for 4 days on the rotary shaker.

The second seed culture in the 5 shake flasks were used to inoculate five 6-liter (L) mini-jars containing 3 L of Medium-2 (glucose 1%, corn starch 2%, NZ amine type A 0.5%, wheat embryo 0.5%, yeast extract 0.5%, $CoCl_2.6H_2O$ 0.00001%, $CaCO_3$ 0.4%, pH 7–7.2). Aeration was carried out at 26° C. for 5 days with 1,700 rpm at 3 L per minute.

After fermentation, the whole mini-jar fermentation broth (15 L) was extracted three times with 15 L of ethyl acetate (EtOAc). The EtOAc layer was dried over $Na_2SO_4$ and concentrated to oily residue. The oily material containing rapamycin was then applied to a fine mesh silica gel (250 g) column which in turn was washed with 1000 ml of n-hexane and 1000 ml of 1:1 n-hexane/EtOAc, and eluted with 1500 ml of 1:2 n-hexane/EtOAc, 1000 ml of EtOAc and finally with 750 ml of 2:1 EtOAc/acetone. Fractions showing the bioactivity were applied to a Sephadex LH-20 (trademark) column and eluted with methanol. The active fractions were concentrated and further applied to a Chemcosorb 5ODS-UH (trademark) column (20 mm×250 mm) eluted with the mixture of methanol and water (4:1) at 5 ml/min. Detection was made by UV absorbance at 305 nm. Finally 4 g of rapamycin was collected by repeating these procedures ten times and the product showed anti-Candida albicans activity.

EXAMPLE 2

A seed culture (5 ml) as described in Example 1 was inoculated into 100 ml of the Medium-2 in a 500-ml shake flask. The flask was shaken at 26° C. for 7 days on a rotary shaker with 7-cm throw at 220 rpm. The production of rapamycin was apparent since the fermentation broth showed anti-Candida albicans activity and the mixed lymphocyte reaction (MLR) activity. The production of rapamycin was confirmed by using HPLC method described as Example 1.

EXAMPLE 3

Actinoplanes sp. N902-109 and Streptomyces hygroscopicus ATCC 29253 were inoculated into each 500-ml shake flask containing 100 ml of the Medium-1 as described in Example 1. These flasks were shaken at 26° C. for 4 days on a rotary shaker with 7-cm throw at 220 rpm. Two each shake flasks containing the same medium (150 ml) were inoculated with each 7.5 ml of the grown culture. These flasks were shaken at 26° C. for 4 days on the rotary shaker.

The seed cultures in the 2 shake flasks were used to inoculate two 6-L fermentation vessels containing 3 L of Medium-3 (glucose 1.5 %, soluble starch 1%, polypeptone 0.5%, molasses 0.5%, lard oil 0.2%, $(NH_4)_2SO_4$ 0.5%, $K_2HPO_4$ 0.5%, $MgSO_4$ 0.025%, $ZnSO_4 \cdot 7H_2O$ 0.005%, $MnSO_4$ 0.001%, $FeSO_4 \cdot 7H_2O$ 0.002%, $CaCO_3$ 0.2%, pH 7.2, which is in accordance with the medium of rapamycin patents, U.S. Pat. No. 3,929,992 and U.S. Pat. No. 3,993,749). Aeration was carried out at 26° C. for 2 to 7 days with 1,700 rpm at 3 L per minute. The fermentation broth samples (50 ml each) which were extracted every day with EtOAc monitored by HPLC as described in Example 1. The highest titers of rapamycin for Actinoplanes sp. N902-109 and Streptomyces hygroscopicus ATCC 29253 were 405 µg/ml (day 6) and 40 µg/ml (day 5), respectively.

We claim:

1. The biologically pure culture Actinoplanes sp. N902-109, FERM BP-3832.

2. A biologically pure culture of Actinoplanes sp. which produces rapamycin in a recoverable amount in an aqueous nutrient medium containing assimilable sources of carbon, nitrogen and inorganic substances, having all of the identifying characteristics of Actinoplanes sp. N902-109.

* * * * *